United States Patent [19]
Stevenson et al.

[11] Patent Number: 5,751,539
[45] Date of Patent: May 12, 1998

[54] EMI FILTER FOR HUMAN IMPLANTABLE HEART DEFIBRILLATORS AND PACEMAKERS

[75] Inventors: Robert A. Stevenson, Canyon Country, Calif.; Dick H. Ni, Carson City, Nev.

[73] Assignee: Maxwell Laboratories, Inc., Carson City, Nev.

[21] Appl. No.: 640,098

[22] Filed: Apr. 30, 1996

[51] Int. Cl.$^6$ ............... H01G 4/35; H01G 4/38
[52] U.S. Cl. ............ 361/302; 174/143; 333/182; 361/330
[58] Field of Search ............ 361/302, 328–330, 361/306.1–306.3, 307; 174/143; 333/182

[56] References Cited

U.S. PATENT DOCUMENTS

| | | |
|---|---|---|
| 3,235,939 | 2/1966 | Rodriguez et al. |
| 3,538,464 | 11/1970 | Walsh. |
| 4,144,509 | 3/1979 | Boutros ............ 361/302 |
| 4,148,003 | 4/1979 | Colburn et al. |
| 4,152,540 | 5/1979 | Duncan et al. |
| 4,424,551 | 1/1984 | Stevenson et al. |
| 5,333,095 | 7/1994 | Stevenson et al. |

*Primary Examiner*—Bot L. Ledynh
*Attorney, Agent, or Firm*—Kelly Bauersfeld Lowry & Kelley, LLP

[57] ABSTRACT

An improved ceramic feedthrough capacitor design which results in distinct advantages in EMI (electromagnetic interference) filtering and therapeutic waveform management for implantable defibrillators and pacemakers and the like. The invention provides ceramic capacitor electrode plate designs which provide both low impedance decoupling for EMI suppression, and, at the same time provide an isolated common ground point through a separate coupling capacitor for electrical isolation of the filtered circuit from the metal case (usually titanium) of the defibrillator or the like. Such an arrangement allows the defibrillator HV (high voltage) output pulse to the heart to be referenced lead to lead (including reverse polarity), or from either lead to a common floating ground point or to the titanium case. The primary application of the invention is directed to implantable defibrillators where the output pulse to the heart is typically high voltage (up to 750 volts) and of short duration (typically in the $10 \times 10^{-3}$ seconds or 10 millisecond range). The invention is equally applicable to implantable pacemakers. The invention is particularly suited for a combination defibrillator (tachycardia) and pacemaker (bradycardia) unit where there are sense (heart monitoring), low voltage (pacing) and high voltage (defibrillator) output leads.

18 Claims, 10 Drawing Sheets

EMI FILTER FOR HUMAN IMPLANTABLE HEART DEFIBRILLATORS AND PACEMAKERS

BACKGROUND OF THE INVENTION

This invention relates generally to improvements in ceramic feedthrough capacitors of the type used in implantable medical devices such as heart pacemakers and the like to decouple undesired interference signals from the device. The leads attaching the implanted device to the heart can act as antennae in the presence of a radiated EMI (electromagnetic interference) field (such as may be generated by cellular telephones).

More particularly, this invention relates to improved ceramic capacitor three terminal electrode plate configurations providing low impedance decoupling for EMI (electromagnetic interference) suppression, in combination with a common ground point through a separate coupling capacitor for electrical isolation of the filter circuit from the metal case of the medical device. The invention is particularly suited for use in defibrillators (tachycardia), heart pacemakers (bradycardia), and combined pacemaker defibrillator devices. Ceramic capacitors are appropriate for this application because of their high unit capacitance provided in a small size with a robust construction.

Ceramic capacitors are typically constructed by interleaving non-conductive layers of high dielectric constant ceramic material with metallic electrodes. The metallic electrodes are typically "laid-down" on the green ceramic material by silk screening processes. The device is then fired (sintered) to form a rigid monolithic structure (the "capacitor").

Well known in the art are feedthrough type monolithic ceramic capacitors, which offer a form factor which provides superior RF (radio frequency) performance for EMI filtering purposes. Reference U.S. Pat. Nos. 4,148,003; 4,152,540; and 3,235,939.

Ceramic feedthrough capacitors have been adapted for EMI filtering of human implant devices (see U.S. Pat. No. 5,333,095). In order to provide proper EMI suppression, it is important that the feedthrough capacitor be directly bonded to the implantable device shield (titanium shell) or hermetic seal. This intimate relationship is essential so that the feedthrough capacitor acts as an integral part of the EMI shield so that undesirable EMI signals are reflected, or absorbed and decoupled before they can enter the interior of the device (inside the titanium shell) where they would disrupt the proper function of sensitive internal electronic circuits.

SUMMARY OF THE INVENTION

In accordance with the invention, the feedthrough capacitor design incorporates novel electrode configurations which allow the internal filtering capacitor elements to be isolated. This allows for flexibility in implantable device (or other applications) waveform management. The preferred installation method for these novel electrode configuration feedthrough capacitors is in accordance with U.S. Pat. Nos. 5,333,095 or 4,424,551, which are incorporated by reference herein. For human implant applications, the feedthrough lead wires are typically platinum, niobium or tantalum for resistance to body fluids. The hermetic terminal to which the feedthrough capacitor is mounted is typically made of titanium-alumina construction with gold brazing or glass sealing for resistance to body fluids.

Advantages of the novel capacitor matrix include:

A. Superior common and differential mode EMI suppression when compared to arrays of rectangular chip capacitors. Feedthrough technology offers greatly improved EMI suppression due to its transmission line type performance (low inductance, high resonant dip, ability to perform above resonance, i.e., broadband performance). Rectangular chip capacitors tend to resonate at a relatively low frequency, and, above resonance they become inductive and cease to function as an effective EMI filter.

B. Fewer components and high volumetric efficiency when compared to an array of monolithic chip capacitors (one feedthrough capacitor with novel electrodes according to the present invention replaces many individual chip capacitors).

C. The implantable defibrillator output waveform may be programmed for alternative circuits while retaining EMI suppression (further described herein).

D. The ability to decouple and suppress EMI right at the terminal-shield interface. This is an important feature when compared to MLC (monolithic capacitor) arrays, particularly when said chips are mounted at a distance from the shield can or housing (titanium). It is really too late to suppress EMI once it is inside of the implantable device housing, usually a shielding titanium case or can. The EMI is often characterized by a very short wavelength which is capable of re-radiating inside the can. The feedthrough type design of the invention actually suppresses the EMI before it enters the can interior where sensitive electronic circuits may be affected.

DETAILED DESCRIPTION OF THE PREFERRED EMBODIMENTS

Figure 1:
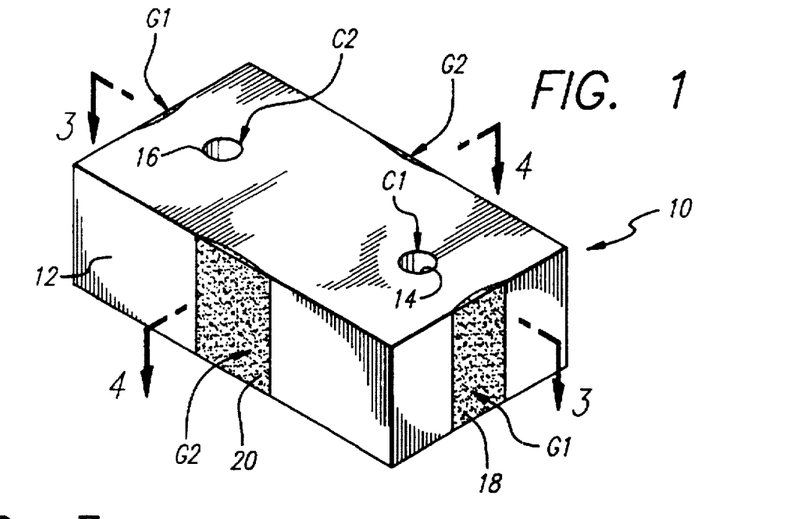
FIG. 1 is an isometric view of a bipolar feedthrough device with two capacitors C1 and C2 shown connected in series with a third capacitor C3, and depicting an isolated ground point (or common test point) G1.

A rectangular bipolar feedthrough capacitor constructed in accordance with the present invention is shown in FIGS. 1 and 3–5. The feedthrough capacitor 10 comprises a multilayered construction having metallic conductive electrode plates arranged in alternating layers of different geometry and separated by dielectric material layers of ceramic or the like. The built-up assembly of multiple ceramic layers with thin metallic electrode plates applied thereto as by silk screening is generally known in the art and will not be discussed in further detail herein. The finished capacitor 10 is depicted in FIG. 1 in the form of a monolithic ceramic structure 12 having the metallic electrode plates embedded therein.

Figure 2:
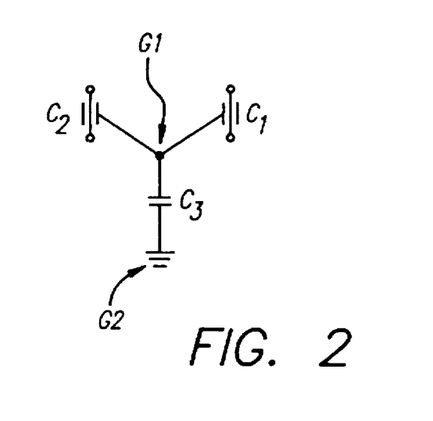
FIG. 2 is a schematic circuit diagram corresponding to the feedthrough device of FIG. 1.

FIG. 1 illustrates the rectangular feedthrough capacitor 10 having a pair of through ports 14 and 16 for receiving a corresponding pair of conductive terminal pins (not shown in FIG. 1). The surfaces of the through ports 14 and 16 are lined by surface metallization, as is known in the art, to connect the plates in parallel and facilitate conductive assembly with the terminal pins. In accordance with the invention, the through port 14 and the surface metallization thereof is conductively associated with a plurality of capacitor electrode plates associated with a first capacitor C1, while the second through port 16 and the surface metallization thereof is associated with a plurality of capacitor electrode plates associated with a second capacitor C2. The two capacitors C1 and C2 are in turn associated with a third capacitor C3 (not shown in FIG. 1) disposed electrically between a pair of electrical connection points G1 and G2 that are exposed by surface metallization 18 and 20, respectively, on discrete edge faces of the ceramic structure 12. FIG. 2 shows an electrical schematic diagram conforming to the bipolar feedthrough capacitor shown in FIG. 1, with the capacitor C3 connecting the two feedthrough capacitors C1 and C2 to a common isolated ground point. It will be understood that the ground point defined at G2 does not represent the ground point of the pulse generator circuit of the medical device, but instead represents the metal housing or shield to which EMI signals are decoupled.

Figure 3:
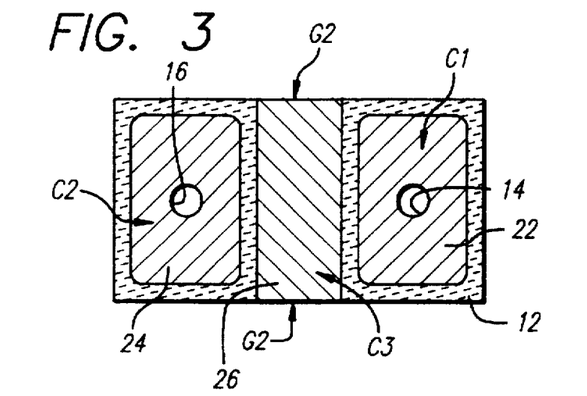
FIGS. 3 and 4 are horizontal sectional views taken generally on the lines 3—3 and 4—4 of FIG. 1.
Figure 4:
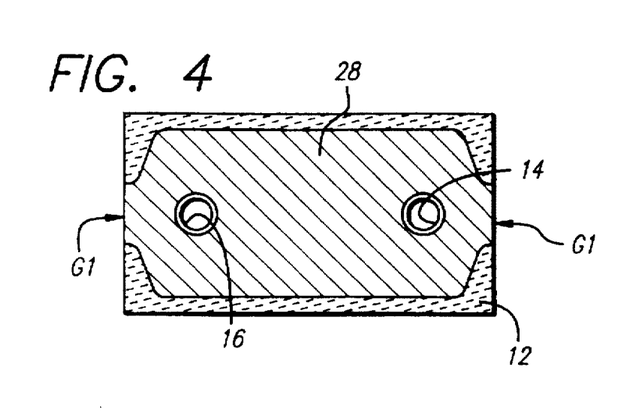
Figure 5:
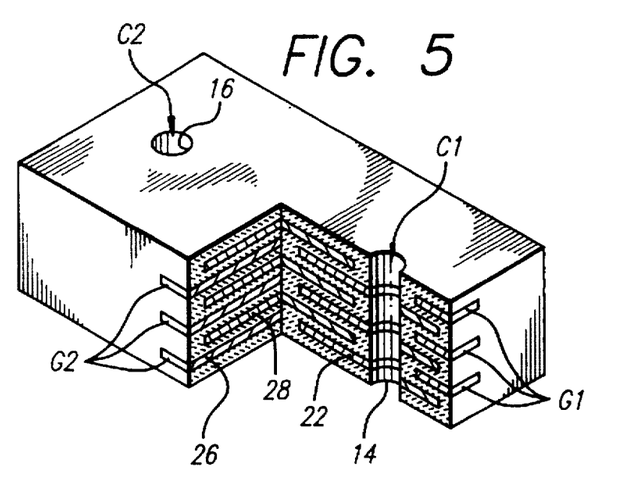
FIG. 5 is a fragmented perspective view of the feedthrough device of FIG. 1, and depicting internal construction details thereof.

FIGS. 3 and 4 are sectional views illustrating alternate layers of metallic conductive electrode plates embedded within the structure of the ceramic body 12. FIG. 3 shows a pair of electrode plates 22 and 24 associated respectively with the through ports 14 and 16, and in electrical isolation with a central plate 26 conforming to the ground point G2. FIG. 4 shows an electrode plate 28 disposed in vertically stacked or sandwiched relation with the electrode plates of FIG. 3, and in electrical isolation to the through ports 14 and 16. When the capacitor 10 shown in FIG. 1 is assembled from a laminated stack-up of alternating plate layers as depicted in FIGS. 3 and 4, and as also depicted in partial section in FIG. 5, the bipolar feedthrough capacitor according to the circuit schematic of FIG. 2 is the result. It will be understood that a typical feedthrough capacitor 10 will incorporate a selected and typically large number of the conductive plate layers shown in FIGS. 3 and 4, in an alternating stack sequence.

Figure 6:
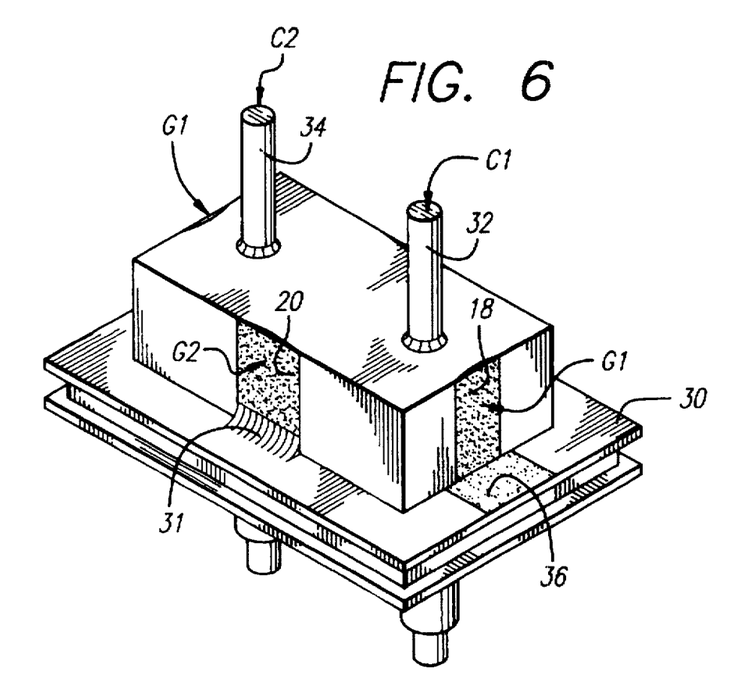
FIG. 6 is a perspective view showing assembly of the feedthrough device of FIG. 1 with a terminal plate adapted for assembly with the housing or can of an implantable medical device.
Figure 7:
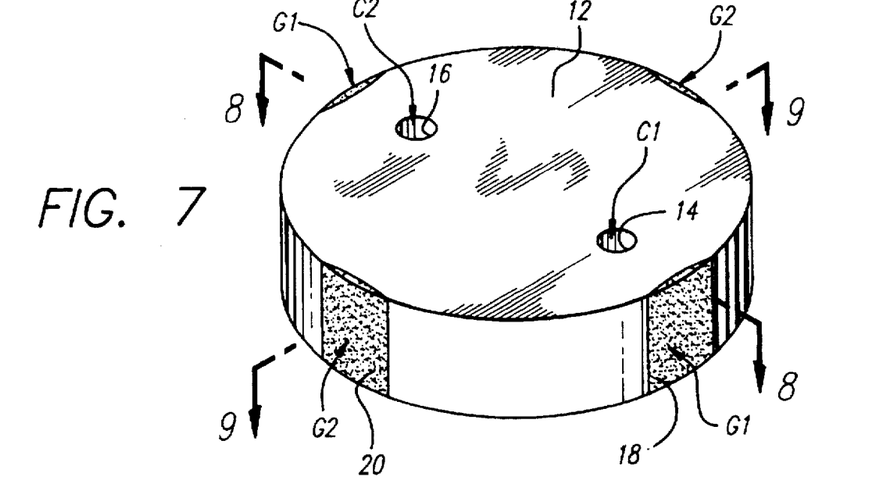
FIG. 7 is an isometric view of an alternative bipolar feedthrough device of discoidal shape, constructed according to the schematic circuit diagram of FIG. 2.
Figures 8, 9:
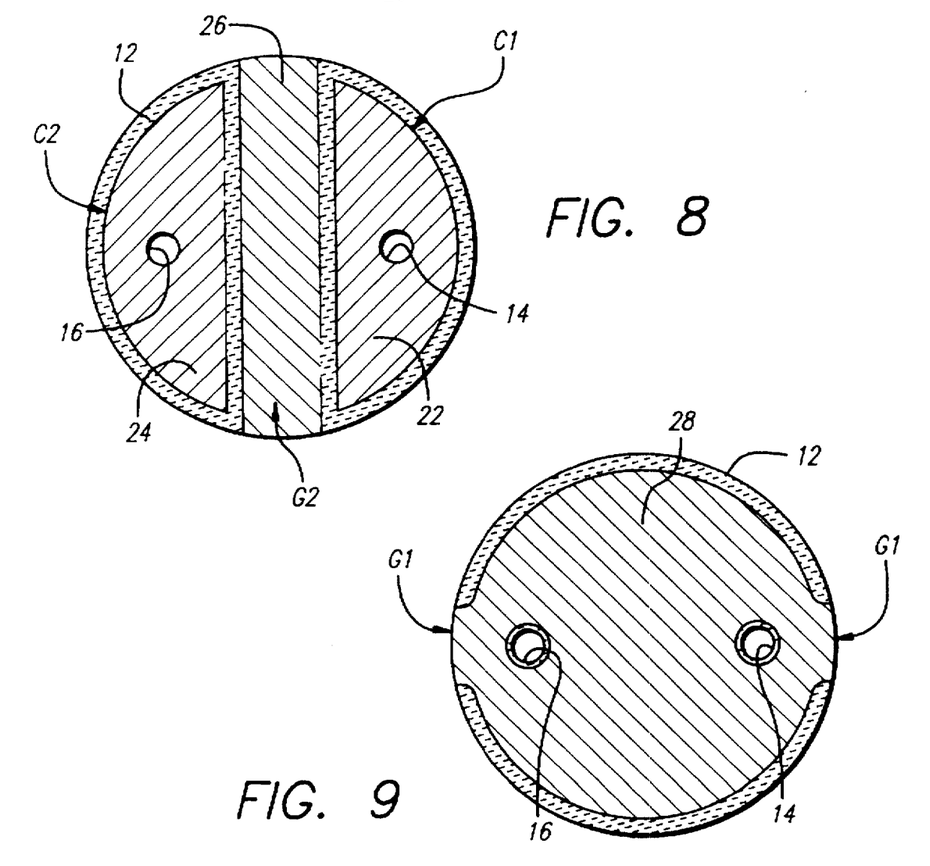
FIGS. 8 and 9 are a horizontal sectional views taken generally on the lines 8—8 and 9—9 of FIG. 7.
Figure 10:
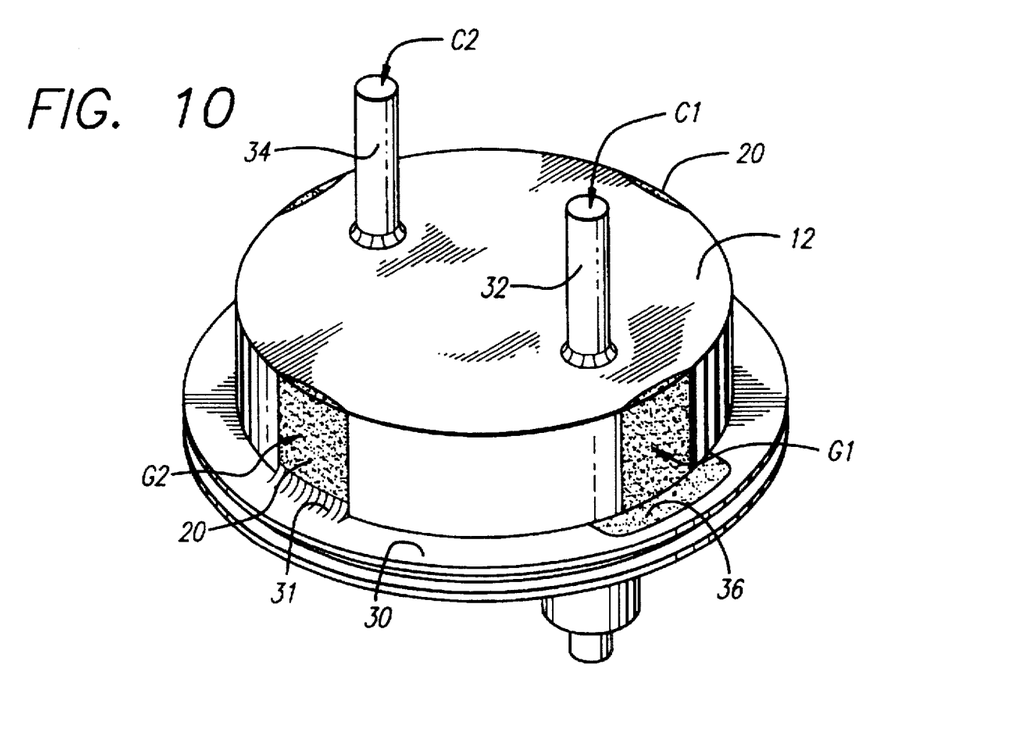
FIG. 10 a perspective view showing assembly of the feedthrough device of FIG. 7 with a terminal plate adapted for assembly with the housing or can of an implantable medical device.
Figure 11:
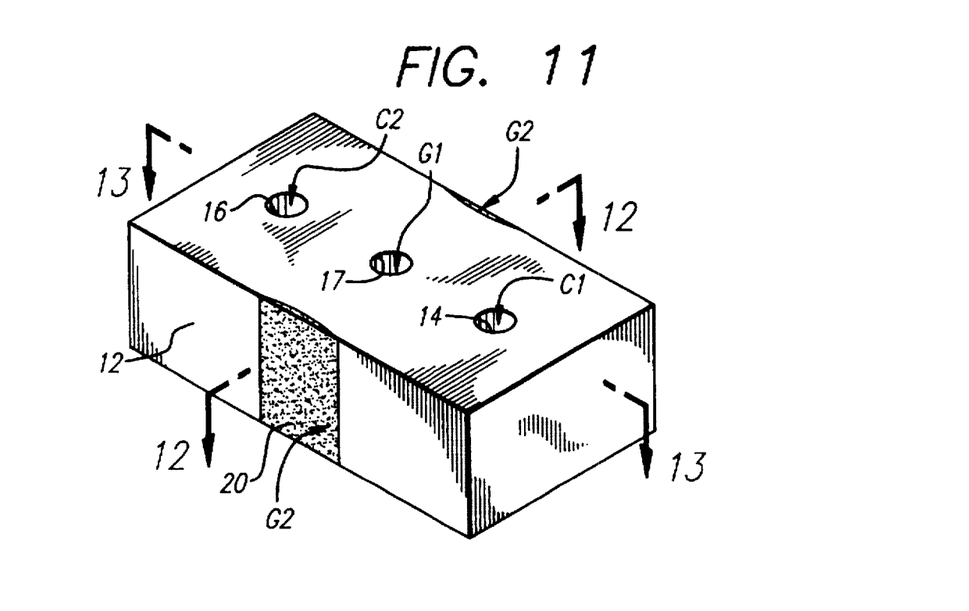
FIG. 11 is an isometric view of another alternative bipolar feedthrough device, constructed according to the schematic circuit diagram of FIG. 2, with a central aperture for connection of the defibrillator pulse generator circuit (not shown) to the isolated ground point G1.
Figures 12, 13:
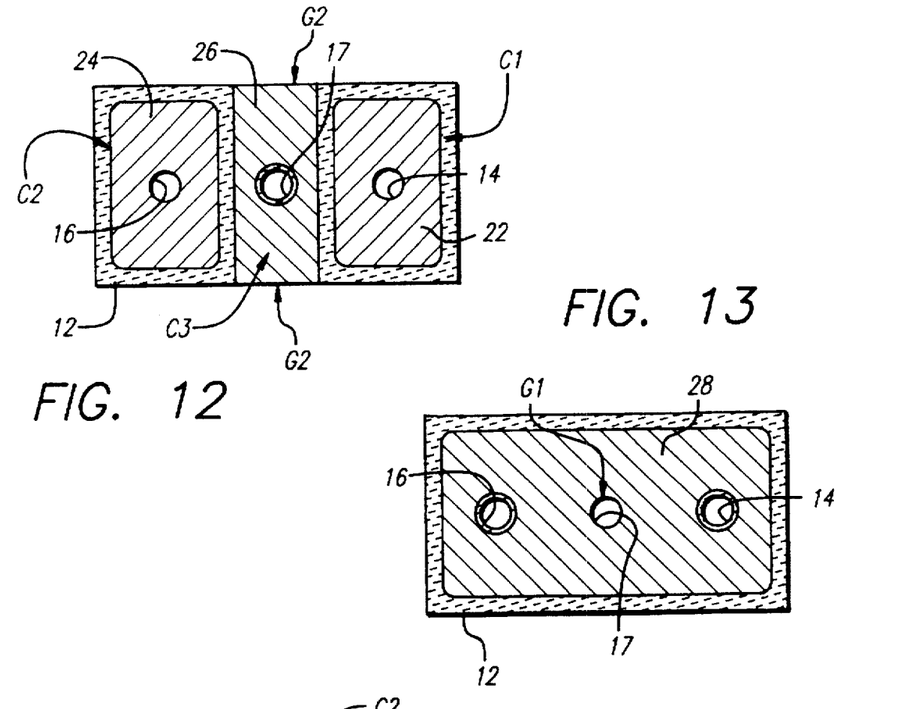
FIGS. 12 and 13 are horizontal sectional views taken generally on the lines 12—12 and 13—13 of FIG. 11.

FIG. 6 shows the feedthrough capacitor 10 of FIGS. 1–5 assembled onto the inboard side of a terminal plate 30 adapted for hermetic and conductive mounting onto the housing of an implantable medical device or the like, so as to position the capacitor 10 within the interior of the housing for the medical device. In the preferred form, the G2 test point or points are designed to be grounded/bonded directly to the terminal plate 30, typically by use of a conductive thermoset material 31 such as conductive polyimide (e.q., Abelstik 71-1). This conductive thermoset material bonds to the G2 capacitor termination surface (typically a palladium-silver glass fired frit) and to the terminal plate 30 as shown. Terminal pins 32 and 34 can be electrically connected to the capacitors C1 and C2 respectively, by means of soldering or alternately by means of the conductive thermoset material. The G1 isolated ground point is desirably insulated from the conductive terminal plate 30 by a suitable insulation sheet 36 or the like. The isolated ground point G1 is accessible for facilitated electrical connection to other circuit components of the medical device or for electrical testing.

FIGS. 7–10 illustrate an alternative preferred form of the invention, wherein structural components conforming to those described in FIGS. 1 and 3–6 are identified by common reference numerals. The embodiment of FIGS. 7–10 differs only in the configuration of the bipolar feedthrough capacitor in a discoidal as opposed to a rectangular geometry.

Figure 14:
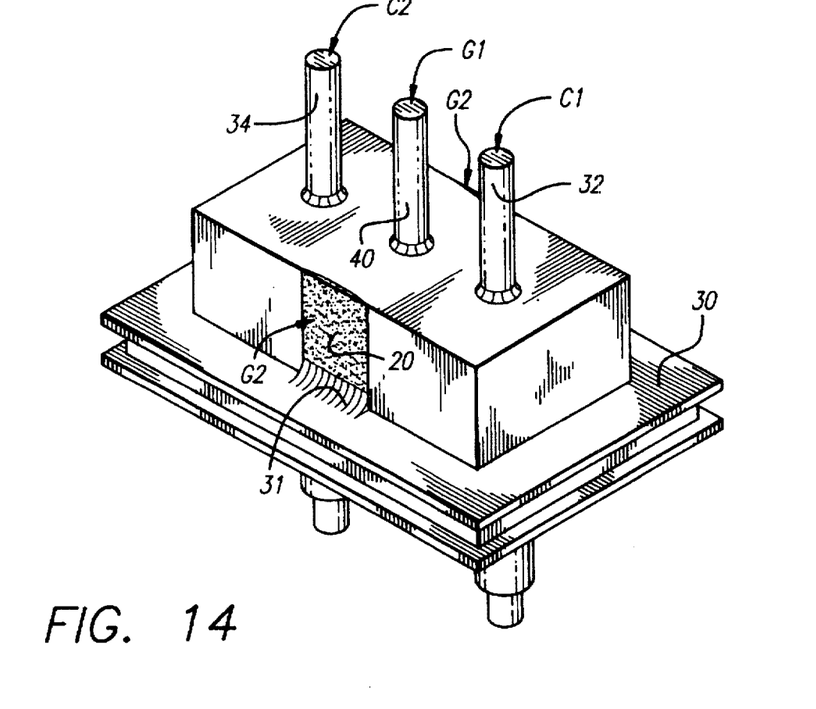
FIG. 14 is a perspective view showing assembly of the feedthrough device of FIG. 11 with a terminal plate adapted for assembly with the housing or can of an implantable medical device.
Figure 15:
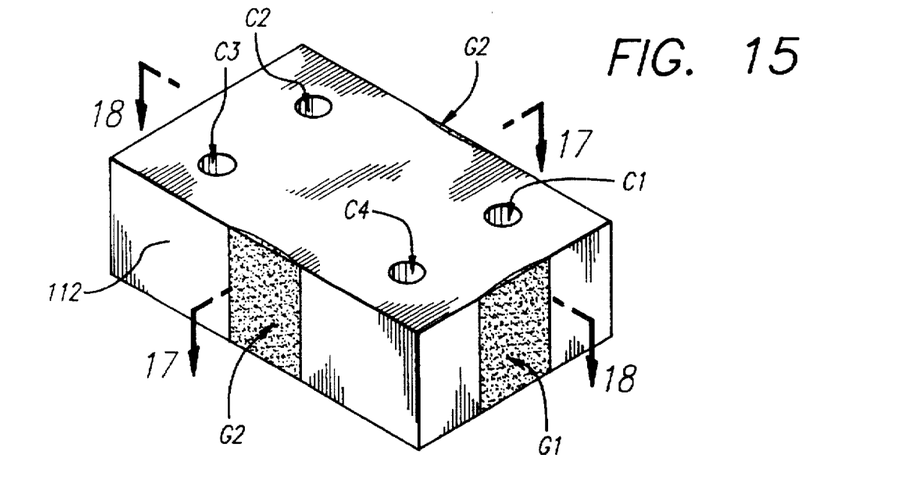
FIG. 15 is an isometric view of a rectangular quad feedthrough device with a common isolated ground point G1.
Figure 16:
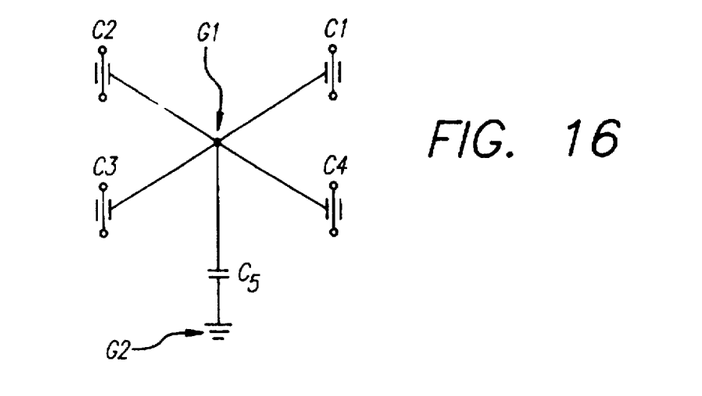
FIG. 16 is a schematic circuit diagram corresponding to the feedthrough device of FIG. 15.

FIGS. 11–14 depict a further alternative preferred form of the invention, wherein components conforming with FIGS. 1 and 3–6 are also identified by the same reference numerals. FIGS. 11–14 show another bipolar feedthrough capacitor, having an alternative rectangular geometry wherein the isolated ground or test point G1 is defined by surface metallization applied to a third through port 17 extending through the capacitor structure 12 at a location between the C1 and C2 capacitor through ports 14 and 16, respectively. As shown in FIG. 14, electrical connection to the isolated ground or test point G1 is accomplished quickly and easily by electrically connecting a third terminal pin 40 thereto. In this embodiment, there is no requirement for additional insulating sheet elements for electrically isolating the test point G1 from the conductive terminal plate 30. Pin 40 typically does not extend all the way through to the body fluid side of the plate 30.

Figure 17:
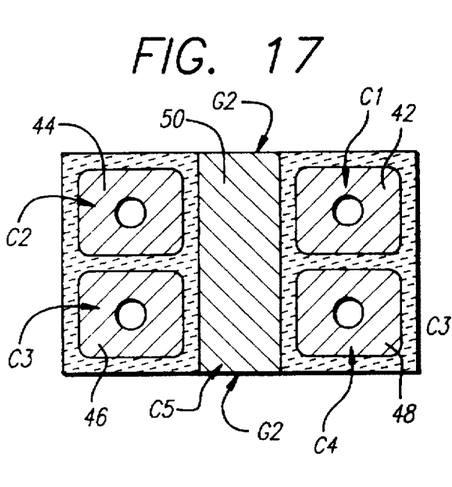
FIGS. 17 and 18 are horizontal sectional views taken generally on the lines 17—17 and 18—18 of FIG. 15.
Figure 18:
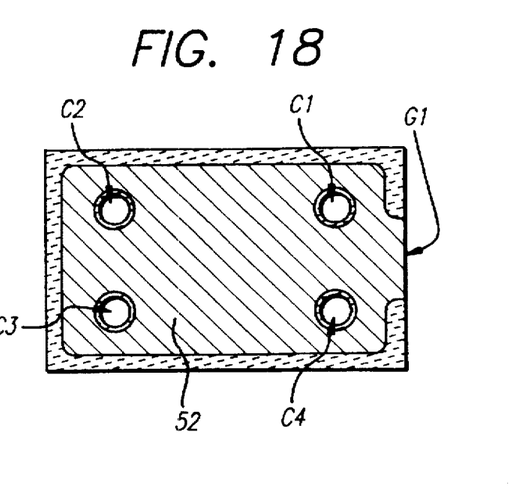

FIGS. 15–18 show a quad-type feedthrough capacitor constructed according to the principles shown and described with respect to FIGS. 1–14. As shown, a multilayer ceramic body 112 has alternating embedded layers of metallic electrode plates in a geometry to provide four separate capacitors C1, C2, C3, and C4 with isolated ground point G1 and ground point G2 including surface metallization on opposite sides of a fifth capacitor C5. This quad feedthrough capacitor is depicted by the circuit schematic of FIG. 16. FIG. 17 shows one layer geometry having active electrode plates 42, 44, 46, and 48 associated respectively with the capacitors C1, C2, C3, and C4, wherein these electrode plates are associated with individual terminal pin through ports lined with surface metallization as previously described. These active electrode plates are arranged in pairs, on opposite sides of a central plate 50 associated with the termination point G2. FIG. 18 shows the electrode plate 52 associated with the test point G1, and formed in electrical isolation with the capacitor terminal pin through ports.

FIGS. 19–22 illustrate an alternative quad feedthrough capacitor with an additional ground point G3 isolated electrically from the isolated ground or test point G1. This alternative feedthrough capacitor is shown in electrical schematic form in FIG. 20 (various alternate schematic configurations are made possible by variations in the printed electrode patterns). Components previously shown and described with respect to FIGS. 15–18 are identified by common reference numerals. The embodiment of FIGS. 19–22 differs only in that the G1 electrode plate 52 is subdivided into a pair of electrode subplates 52A and 52B associated respectively with the electrical connection points G1 and G3. This configuration allows the sense leads (lead wires which monitor the electrical activity of the heart) to be directly decoupled via C2 and C3 (for EMI purposes) to the metallic housing (typically titanium) of the medical device. The sensing circuits are very sensitive and are inherently more prone to disturbance from electrical electromagnetic interference (EMI). The C1 and C4 lead wires may then be used to conduct the high voltage (HV) defibrillator pulse to the heart. Capacitors C1 and C4 are electrically isolated through capacitor C5 from the shield housing of the medical device. This allows the defibrillator pulse to be electrically oriented from lead to lead, from either lead to device housing (case ground), from either lead to G1, or combinations of the above. This output waveform flexibility allows for a wide range of therapeutic options and the restoration of sinus rhythm to the heart.

Figure 23:
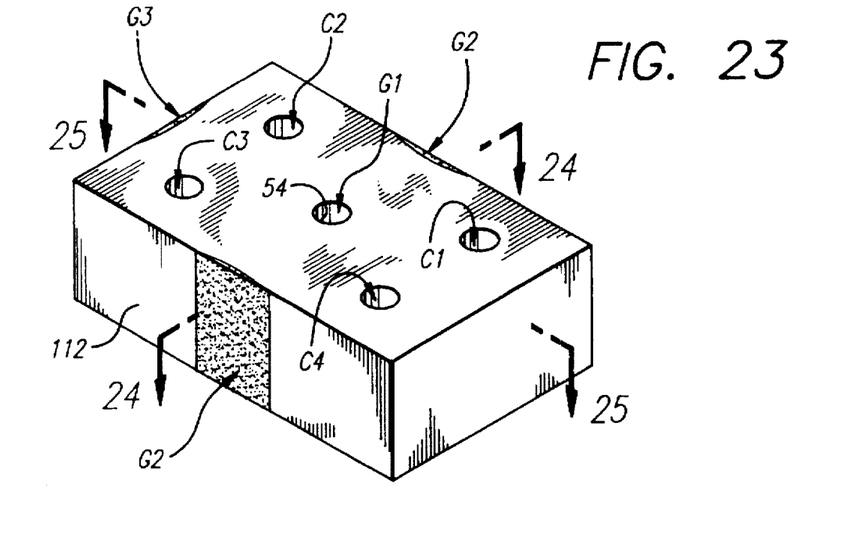
FIG. 23 is an isometric view of a rectangular quad feedthrough device generally according to FIG. 19, but showing an alternative geometry with isolated termination points G1 and G3.
Figure 24:
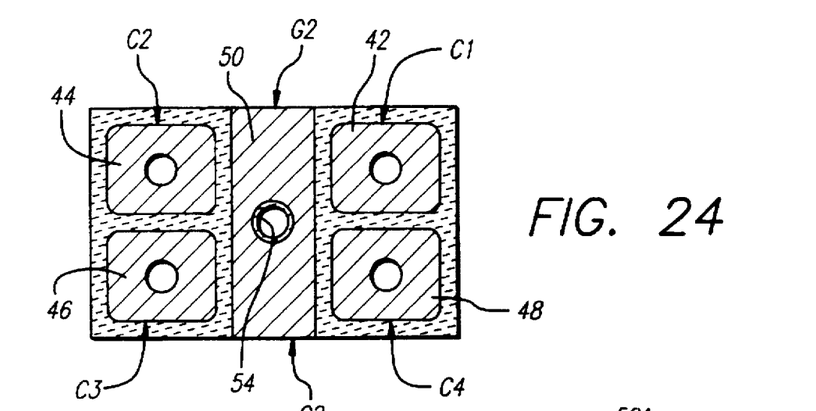
FIGS. 24 and 25 are horizontal sectional views taken generally on the lines 24—24 and 25—25 of FIG. 23.
Figure 25:
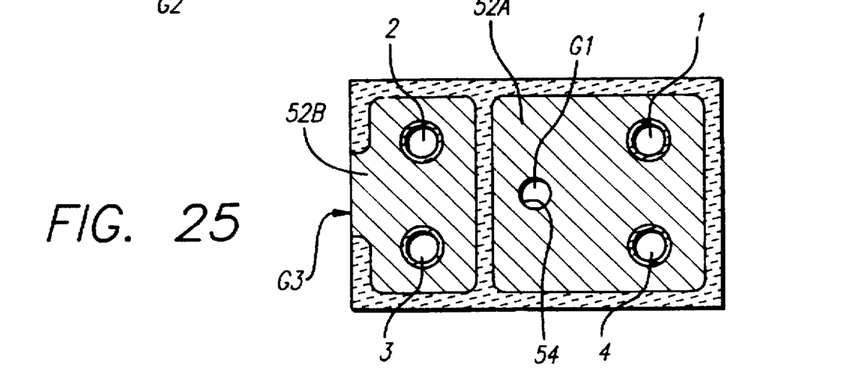
Figure 26:
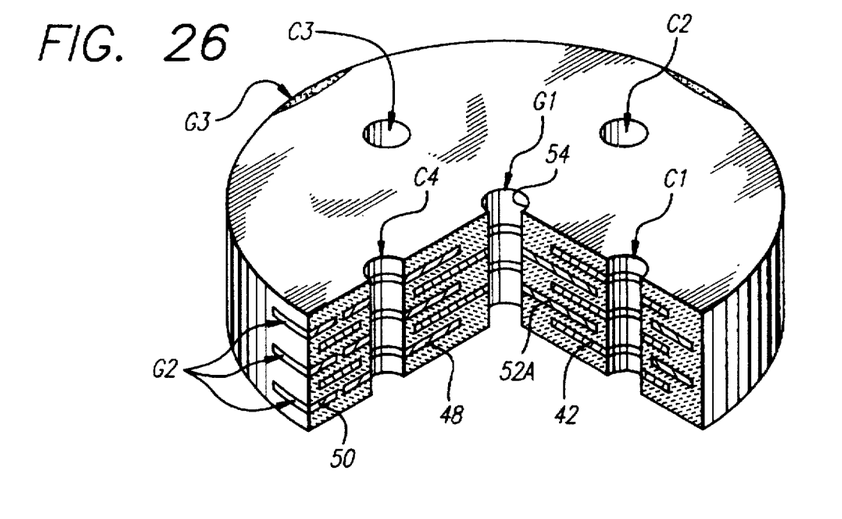
FIG. 26 is a fragmented perspective view of a quad feedthrough device according to FIG. 23, but showing the device in discoidal form.
Figure 27:
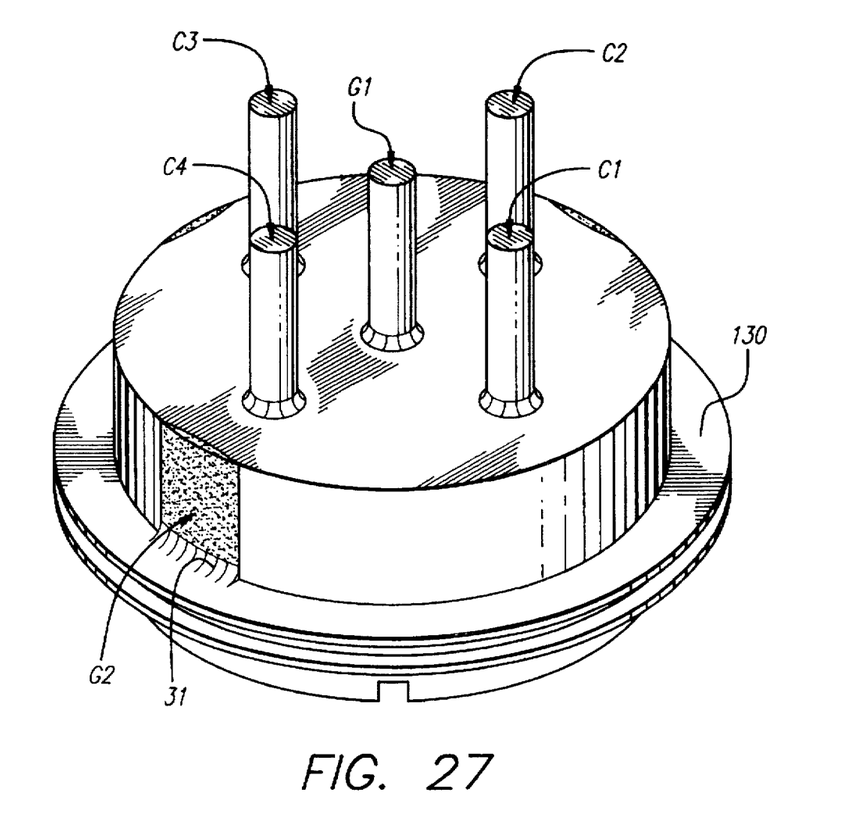
FIG. 27 is a perspective view showing assembly of the feedthrough device of FIG. 26 with a terminal plate adapted for assembly with the housing or can of an implantable medical device.

FIGS. 23–25 show a rectangular quad feedthrough capacitor conforming to FIGS. 19–22, except that the terminal point G1 is defined by surface metallization within a fifth through port 54. FIG. 26 illustrates a quad-type feedthrough capacitor according to FIGS. 23–25, but in discoidal form. FIG. 27 shows the discoidal quad capacitor of FIG. 26 mounted on a conductive terminal plate 130 for appropriate installation onto the typically titanium shield housing of the implantable medical device. Once again, the lead pin associated with the terminal point G1 typically does not extend to through the body fluid side of the assembled device.

Figure 19:
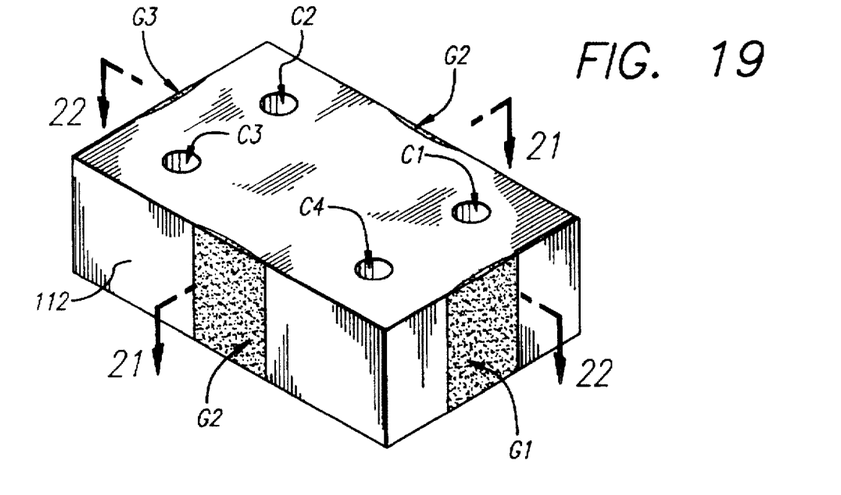
FIG. 19 is an isometric view of a rectangular quad feedthrough device with isolated termination points G1 and G3.
Figure 20:
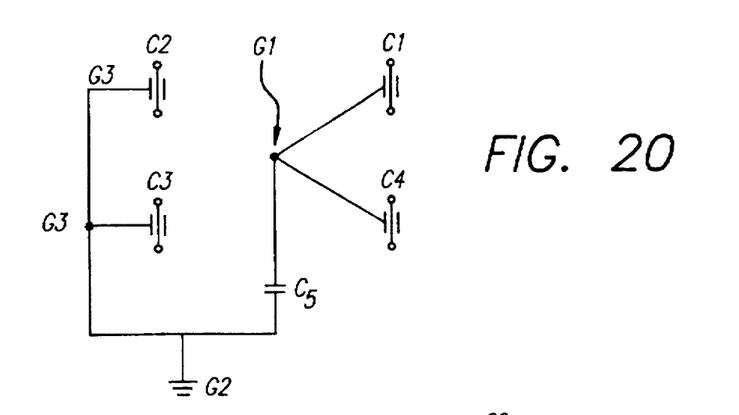
FIG. 20 is a schematic circuit diagram corresponding to the feedthrough device of FIG. 19.
Figure 21:
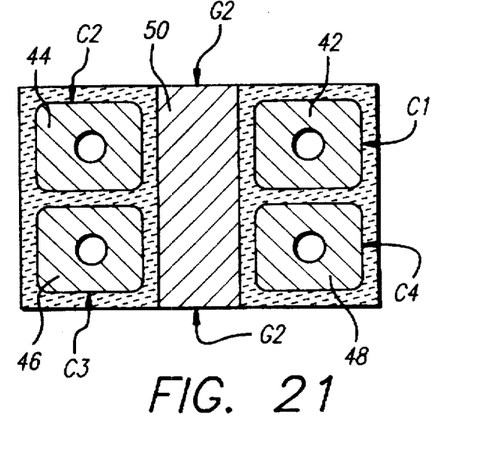
FIGS. 21 and 22 are horizontal sectional views taken generally on the lines 21—21 and 22—22 of FIG. 19.
Figure 22:
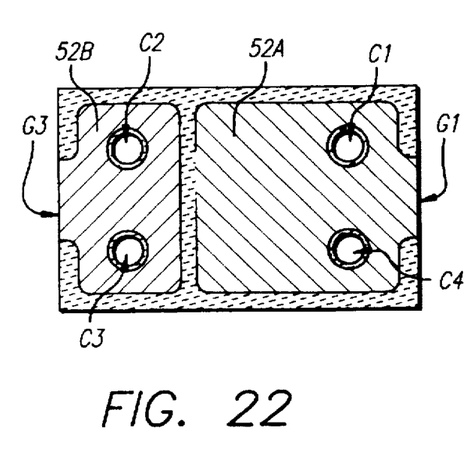
Figure 28:
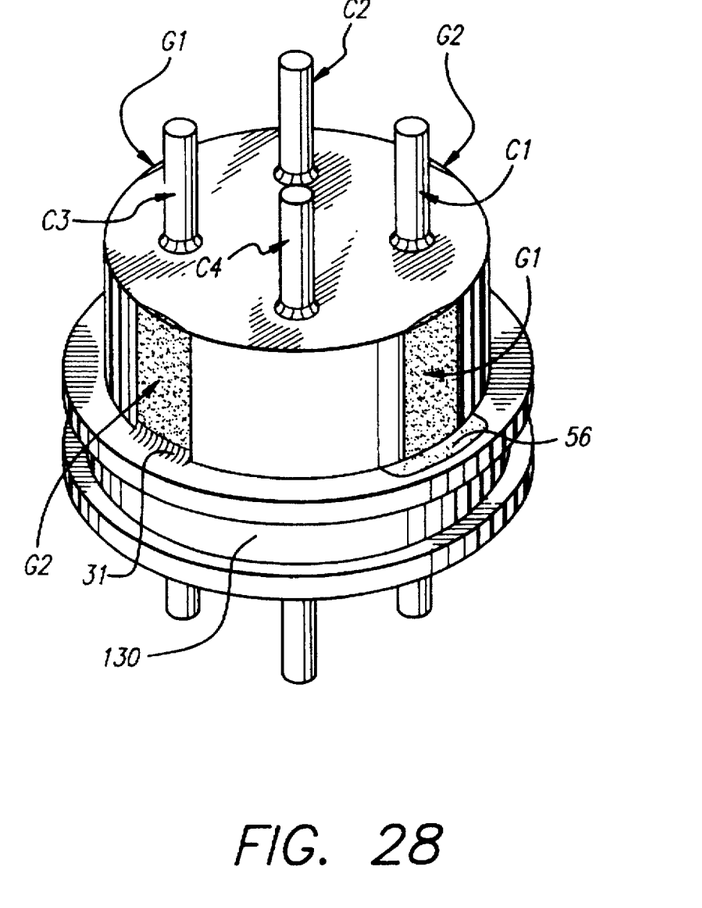
FIG. 28 is a perspective view showing assembly of a feedthrough device generally according to FIG. 19 but in discoidal form with a terminal plate adapted from assembly with the housing or can of an implantable medical device.

FIG. 28 shows an alternative configuration for a quad-type feedthrough capacitor of discoidal geometry, but wherein the terminal point G1 is exposed on the exterior edge of the discoidal capacitor, generally as described with respect to the rectangular quad capacitor of FIG. 19. In this geometry, insulation sheet 56 is required for electrically isolating the termination point G1 from the conductive base plate 130, as shown.

A variety of further modifications and variations to the invention will be apparent to those skilled in the art, such as additional capacitors and lead configurations and the like. For example, it will be understood that the active surface areas of the various conductive plates may be varied to permit selection of specific and proportioned capacitance values, such as variable selection of the active plate areas associated with the plates 22, 24 and 26 shown in FIG. 3. Accordingly, no limitation on the invention is intended by way of the foregoing description and accompanying drawings, except as set forth in the appended claims.

What is claimed is:

1. A feedthrough capacitor assembly, comprising:
   a substantially monolithic casing of dielectric material having a plurality of conductive electrode plates encased therein in an alternating stack of a plurality of first and second layers in spaced parallel relation;
   said first layer including at least one active plate corresponding to at least one feedthrough capacitor, and a first ground plate electrically isolated from said active plate; and
   said second layer including a second ground plate common to said at least one of active plate of said first layer and cooperating therewith to define said feedthrough capacitor, and further cooperating with said first ground plate to define a coupling capacitor for coupling said feedthrough capacitor to a common ground point.

2. The feedthrough capacitor assembly of claim 1 wherein said first layer includes a plurality of electrically isolated active plates corresponding respectively with a selected plurality of feedthrough capacitors, said first ground plate being electrically isolated from said active plates, and said second ground plate of said second layer cooperating with said plurality of active plates to define said plurality of feedthrough capacitors.

3. The feedthrough capacitor assembly of claim 2 wherein said casing has a plurality of through ports formed therein and disposed respectively to expose edges of said plurality of active plates of said first layer.

4. The feedthrough capacitor assembly of claim 3 wherein said through ports are lined with conductive material.

5. The feedthrough capacitor assembly of claim 4 further including a plurality of terminal pins mounted respectively within said through ports.

6. The feedthrough capacitor assembly of claim 2 wherein said casing has a plurality of through ports formed therein and disposed respectively to expose edges of said active plates of said first layer and said second ground plate of said second layer, and first ground plate of said first layer being electrically isolated from said through ports.

7. The feedthrough capacitor assembly of claim 2 wherein said second ground plate of said second layer is subdivided into a pair of electrically isolated subplates, one of said subplates cooperating with a plurality of said active plates to define a plurality of said feedthrough capacitors and cooperating with said first ground plate to define said coupling capacitor, and the other of said subplates cooperating with at least one additional active plate of said first layer to define at least one additional feedthrough capacitor, and means for connecting said other of said subplates directly to said common ground point.

8. The feedthrough capacitor assembly of claim 1 wherein said first layer includes a pair of said active plates corresponding respectively to a pair of said feedthrough capacitors.

9. The feedthrough capacitor assembly of claim 1 wherein said first layer includes at least four of said active plates corresponding respectively to at least four of said feedthrough capacitors.

10. The feedthrough capacitor assembly of claim 1 wherein said casing is formed from a ceramic material.

11. The feedthrough capacitor assembly of claim 1 wherein said casing has a rectangular shape.

12. The feedthrough capacitor assembly of claim 1 wherein said casing has a discoidal shape.

13. The feedthrough capacitor assembly of claim 1 wherein said first ground plate of said first layer is exposed at one edge of said casing.

14. The feedthrough capacitor assembly of claim 13 wherein said second ground plate of said second layer is exposed at one edge of said casing.

15. The feedthrough capacitor assembly of claim 13 wherein said second ground plate of said second layer is exposed within a through port formed in said casing.

16. The feedthrough capacitor assembly of claim 1 wherein said second ground plate of said second layer is exposed within a through port formed in said casing.

17. The feedthrough capacitor assembly of claim 1 further including a conductive terminal plate, said casing being mounted on said terminal plate, and means for electrically connecting said first ground plate of said first layer to said terminal plate.

18. The feedthrough capacitor assembly of claim 17 further including means for isolating said second ground plate of said second layer from said terminal plate.

* * * * *

UNITED STATES PATENT AND TRADEMARK OFFICE
CERTIFICATE OF CORRECTION

PATENT NO.    : 5,751,539
DATED         : May 12, 1998
INVENTOR(S)   : Stevenson et al.

It is certified that error appears in the above-identified patent and that said Letters Patent is hereby corrected as shown below:

Patent Application Serial No. 08/640,098 claims priority from Provisional Application Serial No. 60/007,581, filed November 27, 1995 entitled EMI FILTER FOR HUMAN IMPLANTABLE HEART DEFIBRILLATORS AND PACEMAKERS

Signed and Sealed this

Tenth Day of September, 2002

*Attest:*

*Attesting Officer*

JAMES E. ROGAN
*Director of the United States Patent and Trademark Office*